(12) United States Patent
Molzahn et al.

(10) Patent No.: US 10,150,102 B2
(45) Date of Patent: Dec. 11, 2018

(54) CATALYST REGENERATION PROCESS

(71) Applicant: Dow Global Technologies LLC, Midland, MI (US)

(72) Inventors: David C. Molzahn, Midland, MI (US); Michael L. Tulchinsky, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 164 days.

(21) Appl. No.: 15/125,370

(22) PCT Filed: Feb. 26, 2015

(86) PCT No.: PCT/US2015/017657
§ 371 (c)(1),
(2) Date: Sep. 12, 2016

(87) PCT Pub. No.: WO2015/138129
PCT Pub. Date: Sep. 17, 2015

(65) Prior Publication Data
US 2017/0080408 A1    Mar. 23, 2017

Related U.S. Application Data

(60) Provisional application No. 61/951,770, filed on Mar. 12, 2014.

(51) Int. Cl.

| | | |
|---|---|---|
| *C07D 301/00* | (2006.01) | |
| *C07D 303/22* | (2006.01) | |
| *B01J 23/46* | (2006.01) | |
| *B01J 38/54* | (2006.01) | |
| *B01J 38/70* | (2006.01) | |
| *B01J 23/96* | (2006.01) | |
| *B01J 21/18* | (2006.01) | |
| *B01J 35/00* | (2006.01) | |
| *B01J 35/02* | (2006.01) | |
| *B01J 35/10* | (2006.01) | |

(52) U.S. Cl.
CPC .............. *B01J 23/96* (2013.01); *B01J 21/18* (2013.01); *B01J 23/46* (2013.01); *B01J 23/464* (2013.01); *B01J 38/54* (2013.01); *B01J 38/70* (2013.01); *C07D 301/00* (2013.01); *C07D 303/22* (2013.01); *B01J 35/006* (2013.01); *B01J 35/023* (2013.01); *B01J 35/1019* (2013.01); *B01J 35/1023* (2013.01); *B01J 35/1028* (2013.01); *B01J 35/1061* (2013.01); *Y02P 20/584* (2015.11)

(58) Field of Classification Search
CPC ... B01J 21/18; B01J 23/96; B01J 23/46; B01J 23/464; B01J 35/006; B01J 35/023; B01J 35/1019; B01J 35/1023; B01J 35/1028; B01J 35/1061; C07D 301/00; C07D 303/22; Y02P 20/584
See application file for complete search history.

(56) References Cited

U.S. PATENT DOCUMENTS

| | | | |
|---|---|---|---|
| 3,336,241 A | 8/1967 | Shokal | |
| 3,966,636 A | 6/1976 | Jenkins et al. | |
| 4,847,394 A | 7/1989 | Schuster | |
| 5,530,147 A | 6/1996 | Wettling et al. | |
| 5,614,646 A | 3/1997 | Wettling et al. | |
| 6,130,344 A * | 10/2000 | Hara ................ | C08G 59/1405 549/540 |
| 2004/0176549 A1* | 9/2004 | Bottcher ............... | B01J 23/462 525/507 |
| 2011/0196171 A1* | 8/2011 | Sugawara ............. | C07C 51/36 562/509 |

* cited by examiner

*Primary Examiner* — Timothy R Rozof
(74) *Attorney, Agent, or Firm* — Karl E. Stauss; Cantor Colburn LLP

(57) ABSTRACT

A process for at least partially reactivating the catalytic activity of at least a partially deactivated catalyst following a reaction cycle, the catalyst having been used in a catalytic reaction process for hydrogenating an aromatic epoxide to produce a hydrogenated aliphatic epoxide; said process including contacting the at least partially deactivated catalyst with an oxygen-containing source at a temperature of less than about 100° C. and in the presence of a reactivation solvent for a pre-determined period of time sufficient to at least partially re-oxidize and reactivate the catalyst for further use; and a catalytic reaction process for hydrogenating an aromatic epoxide to produce a hydrogenated aliphatic epoxide including the above reactivating process step; and optionally including a step for washing the deactivated catalyst with a solvent prior to re-oxidizing the deactivated catalyst.

17 Claims, 1 Drawing Sheet

CATALYST REGENERATION PROCESS

FIELD

The present invention is related to a process for regenerating a catalyst after the catalyst has been used in a process for hydrogenating an aromatic epoxide to prepare a hydrogenated epoxide.

BACKGROUND

Catalytic hydrogenation of aromatic epoxy resins, for example, diglycidyl ether of bisphenol A and diglycidyl ether of bisphenol F, produces cycloaliphatic diepoxides. Cycloaliphatic diepoxides are useful as weatherable coatings components in marine coatings, in protective coatings (for example, oil and gas segment, storage tanks, bridges, industrial architecture) and in electronic materials applications.

Catalytic hydrogenation of aromatic epoxides to form cycloaliphatic epoxides can be carried out in one step. However, the challenge for a process of catalytic hydrogenation of aromatic epoxides is the ability to fully (for example, up to about 98% or more) hydrogenate the aromatic rings and at the same time retain the epoxy groups, since epoxy groups can be destroyed by hydrogenation. Heretofore, supported rhodium catalysts have been preferably used in known processes for the catalytic hydrogenation of aromatic epoxides based on the supported rhodium catalysts' high activity (for example, wherein the reaction activity of the catalyst allows for reaction completion within several hours at temperatures of less than about 60° C.) and high selectivity (for example, wherein the reaction selectivity of the catalyst allows for retention of epoxy groups at greater than about 85% at aromatic hydrogenation of greater than about 98%) to cycloaliphatic epoxides.

For example, a cycloaliphatic epoxy resin product can be produced by the hydrogenation of an epoxy resin in the presence of a catalyst and in the presence of a solvent as illustrated by the chemical reaction scheme, Scheme (I), which follows which shows a cycloaliphatic epoxy resin such as a cycloaliphatic diglycidyl ether produced via direct catalytic hydrogenation of a commercial bisphenol A or bisphenol F diglycidyl ether at room temperature (about 25° C.).

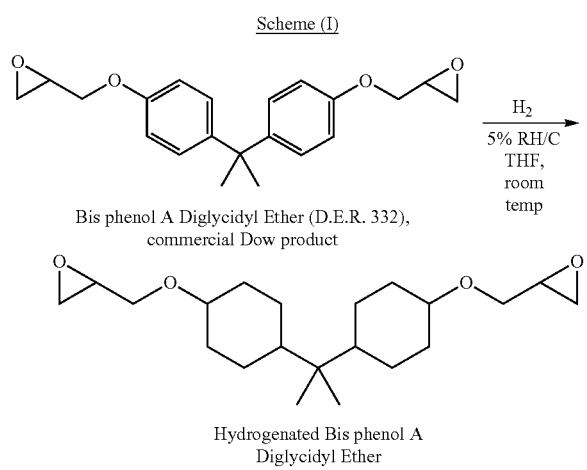

Scheme (I)

Bis phenol A Diglycidyl Ether (D.E.R. 332), commercial Dow product

Hydrogenated Bis phenol A Diglycidyl Ether

A problem with the use of known rhodium catalysts in the above catalytic hydrogenation process is that the catalysts have been found to undergo a rapid deactivation under the process conditions, typically reducing activity twice with every subsequent cycle.

U.S. Pat. No. 3,966,636 discloses a process for the regeneration of a deactivated rhodium (Rh) and ruthenium (Ru) catalyst by sequentially contacting the deactivated catalyst first with a hydrogen-containing gas then with an oxygen-containing gas and finally with a hydrogen-containing gas. In the above process, Rh or Ru supported on an alpha alumina carrier is used as the catalyst; and methylene dichloride ($CH_2Cl_2$) is used as a reactivation solvent. The above patent advocates the use of a multistep and lengthy procedure employing a hydrogen-containing gas at 150° C. to 600° C. and an oxygen-containing gas at 75° C. to 450° C. The complexity and high temperatures employed in the above known procedure makes this approach impractical for reactivating a deactivated catalyst.

US 2011/0196171 A1 discloses a process for producing a hydrogenated aromatic polycarboxylic acid and teaches the use of a primary catalyst of Rh supported on carbon (C) in combination with a secondary catalyst of palladium (Pd) or platinum (Pt) supported on C for the hydrogenation of aromatic carboxylic acids. The method of regenerating the catalyst is carried out by a washing step with water; and the oxidation of the catalyst is carried out by an air oxidation step at room temperature (about 25° C.). The above patent application does not disclose hydrogenating an aromatic epoxide. Also, the examples in the above patent application use water as a solvent; and water is not an acceptable solvent for the aromatic epoxide hydrogenation to aliphatic epoxide due to hydrolysis of epoxy groups in the presence of water.

Other processes for the catalytic hydrogenation of bisphenol A diglycidyl ether are disclosed, for example, in U.S. Pat. Nos. 3,336,241; 4,847,394; 5,530,147; 5,614,646; and 6,130,344; and U.S. Patent Application Publication No. 20040176549. The above prior art, however, does not disclose a suitable process for regenerating a catalyst after the catalyst has been used for hydrogenating bisphenol A diglycidyl ether and related aromatic epoxies. Typically, the catalysts used in the above known processes contain expensive precious metals such as rhodium and/or ruthenium; and a one-time use of such precious metal catalysts is uneconomical.

SUMMARY

In accordance with the present invention, one aspect of the present invention includes a process for re-activating a catalyst. More specifically, the present invention includes a process for re-activating a catalyst which has previously been used in a reaction process for hydrogenating an aromatic epoxide to produce an aliphatic epoxide such as a hydrogenation process for producing a cycloaliphatic epoxy resin. The catalyst of the present invention can include for example a metal catalyst deposited on a carbon support.

It has been surprisingly discovered that catalyst activity can be restored (reactivated) following each reaction cycle for multiple times (for example, at least 10 or more reaction cycles) by using a re-oxidation step or a combination of two or more steps such as for example (a) a catalyst wash step using a specific solvent wash, and (b) a catalyst oxidation step which includes an oxygen-containing gas or air, i.e., the process of the present invention uses air re-oxidation as a step in the re-activation procedure. And, in one preferred embodiment, the regeneration scheme of the present invention catalyst can be performed at a low temperature oxidation such as for example, from about 0° C. to about 100° C. In another preferred embodiment, the reactivation solvent for catalyst re-oxidation can be, for example, methylene dichloride.

Another aspect of the present invention is directed to a catalytic reaction process for hydrogenating an aromatic epoxide to produce an aliphatic epoxide. For example, the aliphatic epoxide produced by the catalytic hydrogenation process of the present invention can be a cycloaliphatic epoxy resin such as a cycloaliphatic diglycidyl ether which can be produced by direct catalytic hydrogenation of an aromatic epoxy resin. The hydrogenation reaction process can include, for example, contacting (reacting) an aromatic epoxy resin with hydrogen in the presence of a metal catalyst and in the presence of a reaction solvent such as tetrahydrofuran (THF) or mixtures of THF and a saturated hydrocarbon such as hexane; wherein after a period of time the catalyst deactivates. The catalyst can then be reactivated by subjecting the catalyst to an oxygen-containing gas or air at a low temperature such as for example from about 0° C. to about 100° C.

In one preferred embodiment, the hydrogenation process of present invention includes carrying out the reaction process at a low temperature, such as for example from about 25° C. to about 50° C., to obtain a high epoxide retention, for example >85%, and overall high reaction selectivity, for example >90%. Advantageously, the reaction process of the present invention is carried out without using water as the solvent, and without employing a secondary catalyst.

Another advantage of the above process of the present invention can include, for example, a simple, less complex procedure for catalyst regeneration without the use of multiple steps if desired. The present invention process is practical and can be used for specific catalysts useful in hydrogenation processes.

BRIEF DESCRIPTION OF THE DRAWINGS

For the purpose of illustrating the present invention, the drawings show a form of the present invention which is presently preferred. However, it should be understood that the present invention is not limited to the embodiments shown in the drawings.

FIG. 1 shows reaction rates declining using the same catalyst loading recycled two times using the same feedstock. The data in FIG. 1 is based on Comparative Example A (22.85 wt % DER 331 hydrogenation in THF at 26.1° C. and 6,200 kPa) and the data in Table I.

FIG. 2 shows that reaction rates can be maintained substantially constant in multiple consecutive hydrogenations using the same catalyst loading when the catalyst is reactivated according to the method of the present invention after each reaction. The data in FIG. 2 is based on Example 1 (22.85 wt % DER 331 hydrogenation in THF at 26.1° C. and 6,200 kPa; and catalyst reactivation by oxidation in $CH_2Cl_2$) and the data in Table II.

DETAILED DESCRIPTION

Figure 1:
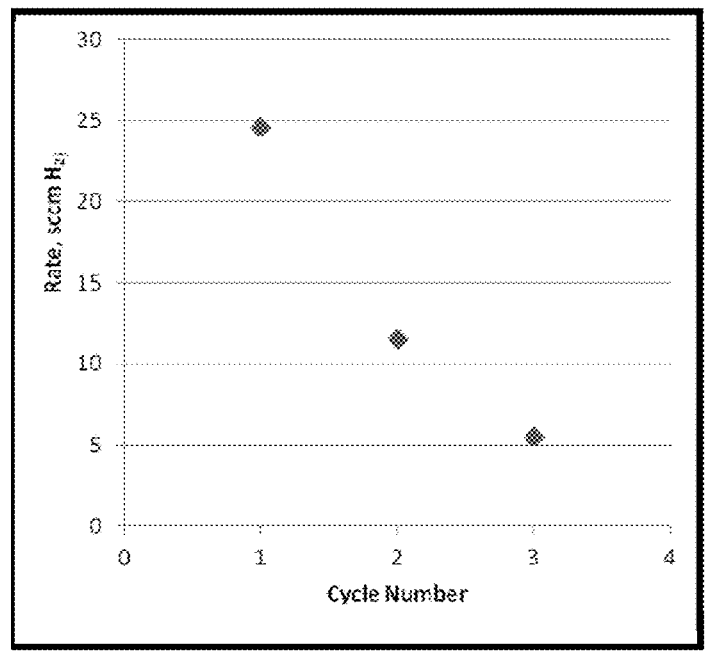
FIG. 1 is graphical illustration showing catalyst deactivation in the absence of a reactivation procedure (i.e., without regeneration of the catalyst) based on the reaction rate of the catalyst versus the number of cycles the catalyst is used.

"Low oxidation temperature" herein, with reference to an oxidation process, means a temperature from about 0° C. to about 100° C.

"Low reaction temperature" herein, with reference to a reaction process, means a temperature from about 0° C. to about 50° C.

"High epoxide retention" herein, with reference to a composition, means that greater than (>) about 85% epoxy groups are remaining intact after hydrogenation of aromatic moieties of an epoxy compound containing epoxy groups.

"High reaction selectivity" herein, with reference to a composition, means that the content of cycloaliphatic diepoxides for an epoxy compound is >about 90%.

A catalyst is typically used in a hydrogenation process, to produce an aliphatic epoxide such as a cycloaliphatic epoxy resin by hydrogenating an aromatic epoxy resin. Generally, the cycloaliphatic epoxy resin is the reaction product resulting from the catalytic hydrogenation of an epoxy resin in the presence of a catalyst and in the presence of a solvent. As aforementioned, a catalytic hydrogenation process for producing the cycloaliphatic epoxy resin product can be illustrated by the above chemical reaction scheme, Scheme (I), which shows a cycloaliphatic epoxy resin such as a cycloaliphatic diglycidyl ether produced via direct catalytic hydrogenation of a commercial bisphenol A or bisphenol F diglycidyl ether.

Once the catalyst in the above catalytic hydrogenation reaction process shows signs of reduced activity, the catalyst can be recovered and reactivated (re-oxidized) for further use in a subsequent hydrogenation reaction step or other processing step.

The reactivated catalyst of the present invention can be used, for example, to further carry out the catalytic hydrogenation process illustrated in Scheme (I) which can include a process for producing a cycloaliphatic epoxy resin such as a cycloaliphatic diglycidyl ether via direct catalytic hydrogenation of an aromatic epoxy resin. Therefore, the hydrogenation process of the present invention can include, for example, reacting
(i) an aromatic epoxy resin with (ii) hydrogen in the presence of (iii) a metal catalyst and in the presence of (iv) a reactivation solvent; wherein the catalyst is reactivated by subjecting the catalyst to an oxygen-containing gas or air at a low temperature and in the presence of a chlorinated solvent.

The epoxy compound useful as the epoxy starting material component to be hydrogenated by the catalytic hydrogenation reaction process may be an aromatic compound having two or more epoxy groups. For example, the epoxy starting material can be bisphenol A diglycidyl ether; bisphenol F diglycidyl ether; a phenol novolac type epoxy resin; a cresol novolak type epoxy resin; hydroquinone diglycidyl ether; resorcinol diglycidyl ether; biphenol diglycidyl ether; 3,3',5,5'-tetramethylbiphenol diglycidyl ether; and mixtures thereof. In one preferred embodiment, the starting epoxy compound can be, for example, bisphenol A diglycidyl ether; bisphenol F diglycidyl ether; or mixtures thereof.

Generally, the concentration of the starting aromatic epoxy is based on the amount of aromatic epoxy in the solvent. The substrate concentration is generally from about 10 wt % to about 50 wt % in one embodiment, and from about 30 to about 40 wt % in another embodiment. If the concentration of the aromatic epoxy is above about 50 wt %, the resultant mixture may be too viscous for a productive reaction; and if the concentration of the aromatic epoxy is below about 10 wt %, a large reactor is required to carry out the hydrogenation reaction.

In general, a low epoxy equivalent weight (EEW) (for example, an EEW of equal or less than about 210) is targeted for the epoxy resins used in the present process. Thus, the amount of the aromatic epoxy resin in the epoxy compound starting material is generally high, for example >about 90%; and a pure aromatic epoxy compound starting material can be for example a starting material with a purity of >about 98%.

The hydrogen ($H_2$) material used for contacting the epoxy compound starting material can be any conventional $H_2$ sources such as a compressed hydrogen gas commercially available in cylinders and commercially supplied for example by Airgas, Inc.

The catalyst compound useful in the process for hydrogenating the epoxy starting material component by the process of the present invention can be for example a metal catalyst deposited on a corresponding solid support or carrier material. The metal catalyst can be selected from the group consisting of rhodium metal, ruthenium metal, a rhodium-containing alloy, a ruthenium-containing alloy, or mixtures thereof.

In one preferred embodiment, the catalyst compound useful for the process of the present invention may include a metal catalyst such as for example Rh supported on a support material or carrier material such as for example carbon. Effective carbon carriers that can be used in the present invention may include for example activated carbon, carbon nanotubes, graphene, and mixtures thereof. Other support materials useful in the present invention include for example alumina, silica, zeolites, or mixtures thereof. The preferred embodiment for the catalyst carrier is activated carbon. The present invention advantageously employs a non-graphite catalyst support material; the non-graphite catalyst support material of the present invention is beneficial because the support material allows for less catalyst deactivation upon reuse.

The percentage of Rh on the support can be generally from about 0.2 wt % to about 50 wt % in one embodiment, from about 0.5 wt % to about 30 wt % in another embodiment; and from about 2 wt % to about 10 wt % in still another embodiment. In another embodiment, the percent Rh dispersion can be from 20% to about 40%. "Percent dispersion" herein is defined as the percentage of all metal atoms in the sample that are exposed.

Although an organic solvent is used in the hydrogenation reaction process, water can be used as a media to measure the acidity/basicity of the catalyst. For example, the pH of the catalyst, as a 5 wt % suspension in water, can be at least about 3 up to less than about 9 in one embodiment; at least about 4 and up to less than about 8 in another embodiment; from about 5 and up to less than about 7 in still another embodiment.

The BET surface area of the support can generally for example at least 100 $m^2/g$ and up to about 1500 $m^2/g$ in one embodiment; at least about 200 $m^2/g$ and up to no more than about 1200 $m^2/g$ in another embodiment; and at least 400 $m^2/g$ and up to about 1,000 $m^2/g$ in still another embodiment.

The mesopore area of the support can be generally for example, at least 75 $m^2/g$ and up to about 750 $m^2/g$ in one embodiment; at least about 100 $m^2/g$ and up to no more than about 500 $m^2/g$ in another embodiment; and at least 200 $m^2/g$ and up to about 400 $m^2/g$ in still another embodiment.

In general, the average particle size of the catalyst can be from about 0.5 nm to about 15 nm in one embodiment, from about 1 nm to about 10 nm in another embodiment, and from about 2 nm to about 9 nm in still another embodiment. In one preferred embodiment, the average Rh particle size can be in the range of from at least about 3 nm up to no more than about 8 nm.

The reaction solvent compound useful in the hydrogenation process can be for example ethers, hydrocarbons, and combinations thereof. In one preferred embodiment, the reaction solvent can be for example dioxane, THF, mixtures of THF with aliphatic hydrocarbons, and combinations thereof. The hydrocarbons can include for example hexane, heptanes, octanes, and mixtures thereof. In one preferred embodiment, the reaction solvent can be for example THF or a mixture of THF and hexane.

Generally, the amount of reaction solvent used in the hydrogenation process should be sufficient to allow for sufficient solubility of the starting aromatic epoxide. For example, a weight ratio of reaction solvent to epoxy may be from 1 to about 10 in one embodiment, from about 2 to about 5 in another embodiment; and from about 2.5 to about 3 in still another embodiment. If the above ratio is greater than 10, the resulting reaction solution can be very dilute which, in turn, can require large reactors, and can make the process inefficient. If the ratio is less than 1, the resulting reaction solution can be too viscous which, in turn, can lead to difficulties in handling the viscous material and carrying out the reaction.

The process for preparing the cycloaliphatic epoxy resin composition via a hydrogenation reaction includes dissolving at least one aromatic epoxy compound in a reaction solvent at the appropriate concentrations, and optionally, any other optional ingredient as desired; and contacting the resultant epoxy solution with a catalyst supported on a carbon carrier under a hydrogen pressure, at a predetermined temperature and a reaction time. Once the reaction is completed, the catalyst is filtered off and the reaction solvent evaporated to provide a hydrogenation product such as a cycloaliphatic epoxy resin composition. The preparation of the cycloaliphatic epoxy resin composition, and/or any of the steps thereof, may be a batch or a continuous process. The equipment employed to carry out the hydrogenation reaction includes equipment known to those skilled in the art.

The hydrogenation reaction is carried out at process conditions to enable the preparation of an effective cycloaliphatic epoxy resin composition having the desired balance of properties for a particular application. For example, generally, the hydrogenation reaction can be carried out at a hydrogen pressure of from about 350 kPa (50 psig) to about 17,000 kPa (2500 psig) in one embodiment; from about 700 kPa (100 psig) to about 14,000 kPa (2000 psig) in another embodiment; and from about 2000 kPa (300 psig) to about 8,000 kPa (1200 psig) in still another embodiment. If a hydrogen pressure below about 350 kPa (50 psig) is used, the reaction may not proceed as desired; and if a hydrogen pressure above about 17,000 kPa (2500 psig) is used, an undesirable over-reduction with opening of the epoxy functionalities may potentially occur.

Generally, the hydrogenation reaction can be carried out at a temperature of from about 0° C. to about 100° C. in one embodiment; from about 0° C. to about 80° C. in another embodiment; from about 20° C. to about 40° C. in still another embodiment; and from about 25° C. to about 35° C. in yet another embodiment. Below a temperature of 0° C., a very slow reaction may occur; and above a temperature of 80° C., a lot of undesirable byproducts may be formed by the process.

The reaction time of the hydrogenation reaction may be generally from about 1 hour to about 24 hours in one embodiment, and from about 3 hours to about 6 hours in another embodiment.

After the reaction ceases and the hydrogenation product (for example, a cycloaliphatic epoxy resin composition product) is produced by the above process, the catalyst used in the process may be separated from the product, for example, by separation techniques known in the art such as by filtration, decantation, centrifugation or combinations thereof to provide a catalyst-free product for further use.

In carrying out the above hydrogenation process using for example the metal catalyst deposited on a carbon support described above, at some point in the hydrogenation process, the catalyst will deactivate and the catalyst will need to be reactivated to reuse the catalyst and continue the hydrogenation reaction to produce reaction product. The present invention provides a process for re-activating the deactivated catalyst which was previously used in the reaction process for hydrogenating an aromatic epoxide. The catalyst reactivation process to restore the catalytic activity of the deactivated catalyst can be carried out after one or more reaction cycles and can include for example subjecting the catalyst to an oxidizing step with oxygen such as an oxygen-containing gas or air stream in the presence of a solvent (herein the "reactivation catalyst).

Accordingly, after the deactivated catalyst is separated from the hydrogenation product by a separation means as described above, the deactivated catalyst is processed through a catalyst reactivation process, i.e., a re-oxidation step.

The catalyst re-oxidation step to regenerate the catalyst can be carried out using various sources of oxygen. For example, the process of re-oxidizing the deactivated catalyst includes using an oxygen source such as pure oxygen, an oxygen source such as an oxygen-containing gas having a predetermined concentration of oxygen, an oxygen source such as air, or any combination thereof. In one preferred embodiment, air, which generally has an oxygen content of about 20%, is used in the catalyst re-oxidation step because air is more economical and safer than using 100% oxygen.

In another embodiment, when an oxygen-containing gas is used as the oxygen source, the oxygen concentration in the oxygen-containing gas can be for example from about 1% to about 100% in one embodiment, from about 10% to about 50% in another embodiment, and from about 15% to about 25% in still another embodiment.

The pressure of oxygen source, for example air, that is used for treating the deactivated catalyst in a solvent can be from 0 kPa to about 7000 kPa (1000 psi) in one embodiment and from 0 kPa to about 3,500 kPa (500 psi) in another embodiment.

The catalyst re-oxidation step to regenerate the catalyst is carried out in the presence of a reactivation solvent. Various reactivation solvents can be used including, for example one or more of the reaction solvents used in the hydrogenation process described above including ethers, hydrocarbons, and combinations thereof. In one preferred embodiment, the reactivation solvent for catalyst re-oxidation can be, for example, methylene dichloride.

The amount of the solvent per 1 g of the spent catalyst can be, for example, from about 5 mL to about 100 mL in one embodiment, from about 10 mL to about 50 mL in another embodiment, and from about 15 mL to about 30 mL in still another embodiment.

The process of re-oxidizing the catalyst may be carried out at a predetermined process conditions such as temperature, pressure and period of time sufficient to reactivate the catalyst. Generally, the set of conditions for reactivating the catalyst can be determined empirically by running a consecutive hydrogenation for a period of time. Usually, up to a time period of 30 minutes at an ambient temperature and ambient pressure is sufficient for catalyst reactivation. For example, the temperature of re-oxidizing the catalyst may be generally from about 0° C. to about 80° C. in one embodiment; from about 10° C. to about 60° C. in another embodiment; and from about 20° C. to about 40° C. in still another embodiment. Running the reaction below room temperature requires cooling and is not practical while running the reaction at temperatures higher than room temperature reduce air solubility in the solvent.

The pressure of re-oxidizing the catalyst may be, for example, generally from about 0 kPa to about 20,000 kPa in one embodiment; from about 0 kPa to about 1,000 kPa in another embodiment; and from about 0 kPa to about 4,000 kPa in still another embodiment.

Generally, the time of re-oxidizing the catalyst may be chosen between about 1 minute to about 2 hours in one embodiment, between about 10 minutes to about 1 hour in another embodiment, and between about 25 minutes to about 1 hour in still another embodiment. Below a period of time of about 1 minute, the time may be too short to ensure sufficient re-oxidation of the catalyst; and above about 2 hours, the time may be too long to be of practical or economical use.

While not wishing to be bound to any particular theory, it is theorized (hypothesized) that the observed results generated from the process of the present invention are obtained because $Rh^{+1}$ present in the Rh/C catalyst (and responsible for high activity) becomes reduced to $Rh^0$ during the hydrogenation process. When the latter is being re-oxidized by air, the catalyst activity recovers. A solvent, such as methylene chloride, is also important for Rh re-oxidation. An additional deactivation mechanism presumably involves catalyst fouling by coating of the catalyst surface with epoxy derived oligomers deposited on the catalyst surface which blocks the catalyst active sites. Methylene dichloride presumably functions as an effective solvent in removing these deposits.

An optional step that can be included in the process of the present invention is a solvent wash step for washing the deactivated catalyst prior to reactivating the deactivated catalyst. The catalyst solvent wash step included as an additional step in the process to regenerate the catalyst can be carried out using various solvents (herein "wash solvent"). For example the wash solvent can include one or more of the same reactivation solvents used in the catalyst re-oxidation step and/or any of the reaction solvents used in the hydrogenation process described above including ethers, hydrocarbons, and combinations thereof. The hydrocarbons used for the wash solvent can also include for example aromatic solvents such as toluene, xylene, benzene or mixtures thereof. In one preferred embodiment, the wash solvent can be a chlorinated hydrocarbon, in particular, methylene dichloride or a mixture of chlorinated hydrocarbons and hydrocarbons such as a methylene chloride-hexane mixture.

The concentration of the wash solvent, when the washing step is used in the present invention, can be for example from 0 wt % to about 80 wt % in one embodiment, from about 10 wt % to about 40 wt % in another embodiment, and from about 20 wt % to about 30 wt % in still another embodiment.

The process of washing the catalyst with a wash solvent may be carried out at a predetermined temperature and for a predetermined period of time sufficient to wash the catalyst. For example, the temperature of washing the catalyst with wash solvent may be generally from about 0° C. to about 80° C. in one embodiment; from about 10° C. to about 80° C. in another embodiment, from about 20° C. to about 80° C. in still another embodiment; and from about 20° C. to about 50° C. in yet another embodiment.

Generally, the washing time for the solvent wash step may be chosen between about 1 minute to about 2 hours in one embodiment, between about 2 minutes to about 1 hour in another embodiment, and between about 5 minutes to about 15 minutes in still another embodiment. Below a period of washing time of about 1 minute, the time may be too short to ensure sufficient washing under conventional washing conditions; and above about 2 hours, the time may be too long to be of practical or economical use.

In one preferred embodiment, the activity and selectivity of the catalyst, after reactivation, should be as close as possible to the original activity and selectivity of the catalyst. In other words, while the reaction rate of a catalyst can depend on particular reaction conditions such as temperature, pressure, solvent, concentration of the starting material, and the like, there is a small difference between the activity and selectivity of a catalyst after regeneration and the original activity and selectivity of the catalyst after several reactions under identical conditions.

For example, the reactivation of the catalyst can be performed such that the difference in activity and selectivity of the catalyst, after reactivation, from the original catalyst is generally within a range of from 0% to less than about 30% of the initial activity and selectivity of the catalyst in one embodiment; from 0% to less than about 20% in another embodiment; from 0% to less than about 10% in still another embodiment; and from 0% to less than about 5% in yet another embodiment. The number of catalyst reuses may depend on how long the catalyst retains its activity and selectivity after reactivation and until other deactivation mechanisms (e.g., attrition, fouling, and the like) take place.

Figure 2:
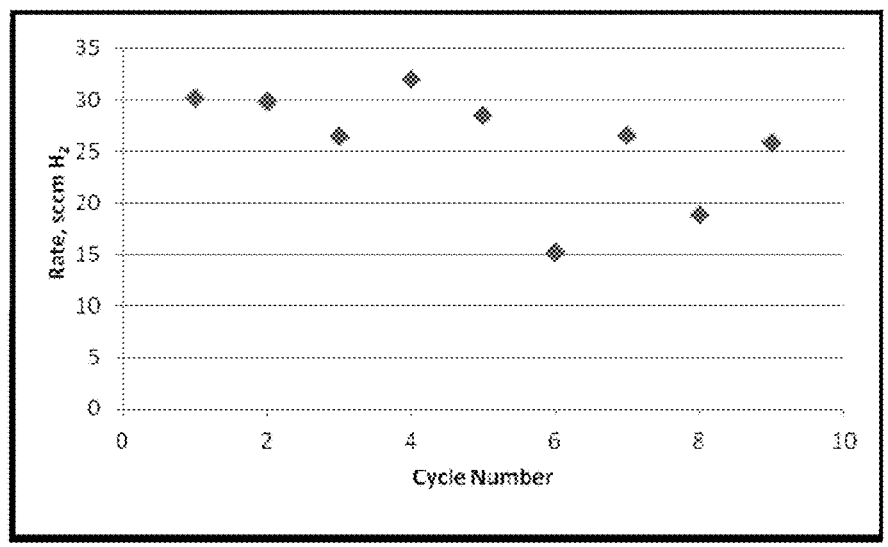
FIG. 2 is graphical illustration showing steady catalyst activity after multiple cycles of use and when a reactivation procedure is used between cycles (i.e., with regeneration of the catalyst) based on the reaction rate of the catalyst versus the number of cycles the catalyst is used.

One of several advantages of the above catalyst regeneration process of the present invention is directed to providing a catalyst that can be reused in multiple reaction cycles. Otherwise, if the catalyst is not reactivated, the catalyst activity decreases quickly and the catalyst becomes unusable, for example after two cycles as illustrated in FIG. 1 and Comparative Example A as compared to many cycles as illustrated in FIG. 2 and Examples 1-4.

EXAMPLES

The following examples and comparative examples further illustrate the present invention in detail but are not to be construed to limit the scope thereof.

Various terms and designations used in the following examples are explained herein below:
"THF" stands for tetrahydrofuran.
"GC" stands for gas chromatography.
"NMR" stands for nuclear magnetic resonance.
"Sccm" stands for standard cubic centimeters.
"ACS" stands for American Chemical Society.
"ACS solvents" are solvents that meet or exceed the specifications set by the American Chemical Society. ACS solvents can be used for applications recommended by ACS or for general procedures that require stringent quality specifications.

"EMD solvents" are high purity grade solvents commercially available from EMD Millipore, the Life Science division of Merck KGaA. EMD solvents can be used in applications required high quality grade solvents.

THF, ACS grade solvents, EMD solvents; methylene chloride, Fisher-Optima are solvents and supplied by Fischer Scientific.

The 5% rhodium on carbon catalyst is commercially available from Strem (Catalog #45-1860).

"Ultra high purity hydrogen" is a high purity grade of hydrogen and commercially available from Michigan Air-Gas.

D.E.R.® 331 is a bisphenol A diglycidyl ether (epoxy resin) with an EEW of 182-192 g/eq and commercially available from The Dow chemical Company.

Standard analytical equipments and methods are used in the Examples including: a Gas Chromatograph 6890 (Agilent Technologies) and a Nuclear Magnetic Resonance spectrometer Varian 400 MHz.

General Procedure for Reaction Process

The reactions, in the examples which follow, were run in a 300 mL stainless steel Parr pressure vessel (reactor) with a magnetically coupled overhead stirrer. The standard stirring speed was approximately 1200 revolutions per minute (rpm). Hydrogen was added to the reactor through a Brooks mass flow controller, model 5850, and the total amount of hydrogen added to the reactor was digitally integrated using a software macro with an update frequency of one second. Reactants were loaded into the reactor and the reactor was sealed and placed into a reactor stand. The reactor was pressure tested with nitrogen. The nitrogen was vented and the reactor was filled with hydrogen to the desired operating pressure. The pressure was allowed to decrease to 70 kPa (10 psig) less than the pressure set-point before hydrogen was added to the reactor to bring the pressure back up to the set-point.

The reactions, in the examples which follow, were analyzed based on the initial hydrogen uptake rate (generally, over the first 60 minutes of the reaction), the total consumption of hydrogen, and the GC and NMR analysis of the liquid reaction product. In the GC analysis, there can be seen three major product peaks for fully hydrogenated bisphenol A diglycidyl ether (H-12 D.E.R. 331) including cis-cis, cis-trans and trans-trans; and two major peaks for half-hydrogenated bisphenol A diglycidyl ether, with only one aromatic ring hydrogenated (H-6 D.E.R. 331) including cis and trans.

Gas Chromatographic Analysis

In the examples which follow, gas chromatographic analysis was performed using a Hewlett-Packard 6890 GC with a 15 m DB-5 (0.32 mm internal diameter, 0.1 micron) column. The inlet temperature of the above GC instrument was 220° C. Thermal decomposition of starting D.E.R. 331 was noted with higher injection temperatures. The oven of the above GC instrument was heated to an initial oven temperature of 50° C. and held at this temperature for 2 minutes (min). Thereafter, the oven temperature was increased at 20° C./min to a final temperature of 250° C. The oven was held at the final temperature for 18 min. Reaction samples were diluted to about 5 weight percent solids with acetone and the injection size was one microliter with a 20/1 split. All GC results are reported based on area percent analysis with the solvent peaks excluded. The following equations were used:

$$\text{Conversion (based on } H_2 \text{ uptake)} = \frac{(\text{Total } H_2 \text{ final} - \text{Total } H_2 \text{ initial})}{6*22415*(\text{wt } D.E.R \ 331)/340.17}$$

GC Conversion estimate =

[Area % $H - 12$ $D.E.R.$ 331 + 0.5*(Area % $H - 6$ $D.E.R.$ 331)]

Epoxy Equivalent Weight Determination

Epoxy equivalent weight (EEW) measurements are performed as follows. The material (0.2 g) is dissolved in methylene chloride (15 mL) and tetraethyl ammonium bromide (15 mL) with stirring provided by a magnetic stirrer. To the stirring solution is added 3 drops of the crystal violet indicator solution (0.1% w/v). Upon solution of the indicator the mixture is titrated with 0.1N perchloric acid in acetic acid until the endpoint is observed by transition from purple to blue green to green (transition may be very quick). The % epoxide=[(ml of titrated sample)–(ml of titrated blank)] *0.4303/grams of material and the epoxy equivalent weight (EEW)=4303/% epoxide.

Comparative Examples A—Hydrogenation of Bisphenol a Diglycidyl Ether without Catalyst Reactivation The pressure vessel (or reactor) was loaded with 100 g of 22.8 wt % D.E.R. 331 in THF and 2.0 g of Rh/C catalyst (Strem 45-1860, Lot 19279100). The pressure vessel was sealed and then placed into the reactor stand. The vessel was pressurized to 5,500 kPa (800 psig) with nitrogen to test for leaks. The reactor was not leaking and the nitrogen was vented. The reactor was pressurized with hydrogen to 6,200 kPa (900 psig). The reaction was run with a temperature set-point of 25° C. and the average temperature for the run was 26.1° C. The reaction was run for 600 min. At the end of this run (cycle #1), the reactor was vented, then closed, and then removed from the reactor stand to a nitrogen atmosphere glove box. The catalyst was recovered in the glove box by vacuum filtration.

The used catalyst was returned to the pressure vessel. The pressure vessel was then loaded with 100.5 g of 22.8 wt % D.E.R. 331 in THF. The reactor was sealed inside the glove box and then the reactor was placed into the reactor stand. The pressure vessel was leak tested with nitrogen at 5,500 kPa (800 psig). The nitrogen was then vented from the vessel; and then the vessel was pressurized with hydrogen at 6,200 kPa (900 psig). The reaction was run with a temperature set-point of 25° C. for 1440 min. The average reaction temperature was 25.4° C. At the end of this run (cycle #2), the reactor was vented, then closed, and then removed from the reactor stand to a nitrogen atmosphere glove box. The catalyst was recovered in the glove box by vacuum filtration.

The used catalyst was returned to the pressure vessel. The pressure vessel was then loaded with 100.0 g of 22.8 wt % D.E.R. 331 in THF. The reactor was sealed inside the glove box and then the reactor was placed into the reactor stand. The reactor was leak tested with nitrogen at 5,500 kPa (800 psig). The nitrogen was vented from the vessel and then the vessel was pressurized with hydrogen at 6,200 kPa (900 psig). The reaction was run with a temperature set-point of 25° C. for 1258 min. The average reaction temperature was 25.5° C. At the end of this run (cycle #3), the reactor was vented, then closed and then removed from the reactor stand to a nitrogen atmosphere glove box. The catalyst was recovered in the glove box by vacuum filtration. The data described in Table I show that more than 50% activity of the catalyst was lost for each reuse.

TABLE I

5% Rh/C Catalyst Deactivation in THF at 26.1° C., 6,200 kPa (900 psig)

| Cycle # | Rate (sccm $H_2$) | ° C. (average) | Rate* (sccm $H_2$ @ 26.1° C.) |
|---|---|---|---|
| 1 | 24.6 | 26.12 | 24.6 |
| 2 | 11.0 | 25.40 | 11.5 |
| 3 | 5.3 | 25.54 | 5.5 |

*The corrected rate assuming the same reaction temperature.

Example 1—Hydrogenation of Bisphenol a Diglycidyl Ether with Catalyst Reactivation The pressure vessel was loaded with 100 g of 22.8 wt % D.E.R. 331 in THF and 2.00 g of Rh/C catalyst (Strem 45-1860, Lot 19279100). The pressure vessel was sealed and then placed into the reactor stand. The vessel was pressurized to 5,500 kPa (800 psig) with nitrogen to test for leaks. The reactor was not leaking and the nitrogen was vented. The reactor was then pressurized with hydrogen to 6,200 kPa (900 psig). The reaction was run with a temperature set-point of 25° C. and the average temperature for the run was 26.1° C. The reaction was run for 400 min. At the end of this run (cycle #1), the reactor was vented, then closed, and then removed from the reactor stand to a nitrogen atmosphere glove box. The catalyst was recovered by filtration through a medium fritted glass filter in a laboratory hood. After filtration the catalyst was placed into a beaker and combined with methylene chloride. The resultant slurry was stirred for 30 min (in air), and then the catalyst was collected by filtration. The solid catalyst on the fritted glass filter was washed with additional portions of methylene chloride, and then air dried on the fritted glass filter. The dried catalyst weight was 1.92 g.

The catalyst was loaded in to the Parr reactor and then 104.4 g of 22.8% D.E.R. 331 in THF was added to the reactor. The reactor was sealed and then placed into the reactor stand. The reactor was tested for leaks with nitrogen at 5,500 kPa (800 psig). The nitrogen was then vented from the vessel and then the vessel was pressurized with hydrogen at 6,200 kPa (900 psig). The reaction was run with a temperature set-point of 25° C. for 600 min. At the end of this run (cycle #2), the catalyst recovery procedure was repeated. The catalyst was tested an additional 7 more times for a total of nine times (i.e., the catalyst was processed through a total of 9 cycles using the above procedure).

The basic procedure above was used for cycles #1-3. The basic procedure used for cycles #1-3 was slightly modified for cycles #4-9 as follows:

(a) For cycle #4, fresh catalyst (0.21 g) was added to the recovered catalyst (1.80 g).

(b) For cycle #5, fresh catalyst (0.15 g) was added to the recovered catalyst (1.85 g).

(c) For cycle #6, at the end of the cycle, the catalyst was washed with methylene chloride in the nitrogen glove box and not exposed to air.

(d) For cycle #7, the catalyst used for this cycle was washed with methylene chloride in the glove box and not exposed to air. At the end of this cycle, the catalyst was washed with methylene chloride on the filter and then the catalyst was vacuum dried at 70° C.

(e) For cycle #8, water (0.354 g) was added to the cycle.

(f) For cycle #9, the D.E.R. 331/THF mixture was 112.6 g instead of 100 g.

TABLE II

Reuse of 5% Rh/C After Reactivation Using $CH_2Cl_2$ Wash and Air Exposure for the Hydrogenation of Bisphenol A Diglycidyl Ether (D.E.R. 331) in THF

| Cycle # | Rate (uptake in sccm at temperature in ° C.) | Regeneration/ Conditions | Comments |
|---|---|---|---|
| 1 | 30.2 @26.1 | Fresh catalyst in THF | Standard cycle |
| 2 | 29.8 @26.1 | $CH_2Cl_2$, wash with air exposure | |
| 3 | 26.5 @26.1 | $CH_2Cl_2$, wash with air exposure | |
| 4 | 32.0 @27.7 | $CH_2Cl_2$, wash with air exposure | Corrected to 28.7 @26.1° C. |
| 5 | 28.5 @26.2 | $CH_2Cl_2$, wash with air exposure | |
| 6 | 15.2 @26.1 | $CH_2Cl_2$, nitrogen box wash | |
| 7 | 26.6 @26.1 | $CH_2Cl_2$, wash with air exposure | Vacuum dried @70° C. |
| 8 | 18.9 @ 26.1 | $CH_2Cl_2$, nitrogen box wash + 0.35 g $H_2O$ | |
| 9 | 25.9 @ 26.1 | $CH_2Cl_2$, wash with air exposure | Excess feed 12.6 g |

The data in Table II above show that less than overall 15% activity of the catalyst was lost after the 9 reuses of catalyst. As shown in cycle #6, when the catalyst is washed with methylene chloride only without air exposure, re-activation of the catalyst is poor. However, over the nine cycles described in Table II, the results show that the methylene chloride wash with air exposure greatly improves the catalyst re-usability (e.g., compare Example 1 with Comparative Example A).

Example 2—Batch Process at 8,300 kPa (1200 Psi) with Catalyst Reactivation Inside a Reactor Under Pressure Bisphenol A diglycidyl ether (D.E.R. 331, 30.6 g; 90 mmol) in anhydrous THF (60 mL) was charged into a 250 mL Parr reactor along with 3.0 g of 5% Rh/C from Strem. The resulting system was purged with hydrogen three times at room temperature (about 25° C.) at about 700 kPa (100 psi). The reaction was carried out at room temperature and 8,300 kPa (1,200 psi) of hydrogen. When the hydrogenation reaction was completed based on GC/NMR, the reaction mixture was filtered using an internal filter in the reactor, the catalyst inside the reactor was rinsed one time with methylene chloride (60 mL) with stirring and then the solvent was removed via the internal filter. Then, methylene chloride (60 mL) was added to the reactor; and the reactor was pressurized with air at 3,400 kPa (500 psi) and stirred for 30 min. The solvent was filtered off and a new loading of D.E.R. 331 in THF was introduced into the reactor to start a consecutive reaction.

Table III illustrates that catalyst reactivation inside the reactor with air in methylene chloride under pressure is effective while reactivation with toluene is not. The reactions shown in Table III were run at 25° C. (room temperature).

TABLE III

| Cycle # | Reaction Time (hours) | Hydrogenation (% by NMR) | Epoxy equivalent weight (EEW) (g/eq) | Catalyst Treatment, ($CH_2Cl_2$/Air), 3,400 kPa (500 psi) |
|---|---|---|---|---|
| 1 | 4 | 98.9 | 210 | Fresh |
| 2 | 6 | 99.1 | — | Air 3,400 kPa (500 psi) |
| 3 | 6 | 99.5 | — | Air 3,400 kPa (500 psi) |
| 4 | 6 | 99.2 | 200 | Air 3,400 kPa (500 psi) |
| 5 | 8 | 98.2 | — | Air 1000 kPa (150 psi) |
| 6 | 5 | 99.2 | — | Air 3,400 kPa (500 psi) |
| 7 | 6 | 99.4 | 201 | Air 3,400 kPa (500 psi) |
| 8 | 6 | GC data | — | Air 3,400 kPa (500 psi) |
| 9 | 6 | GC data | — | Air 3,400 kPa (500 psi) |
| 10 | 7 | 98.9 | 209 | Air 3,400 kPa (500 psi) |
| 11 | 8 | GC data | — | Air 3,400 kPa (500 psi) |
| 12 | 6 | GC data | — | Air 3,400 kPa (500 psi)/ 50° C. |
| 13 | 10 | GC data | — | Toluene in place of $CH_2Cl_2$, 3,400 kPa (500 psi)/50° C. |
| 14 | 7 | GC data | — | Air 3,400 kPa (500 psi)/ 50° C. |

Example 3—Batch Process at 4,100 kPa (600 Psi) with Catalyst Reactivation Inside a Reactor Under Pressure A catalyst, 5% Rh/C from Strem (2.0 g), was placed into a 250 mL Parr reactor and rinsed with anhydrous THF (40 mL) solvent. The THF solvent was filtered and hexane-methylene chloride solvent 1:1 (40 mL) was added to the reactor. The resultant mixture was stirred at 3,400 kPa (500 psi) air for 30 min. Then, the hexane-methylene chloride solvent was filtered and D.E.R. 331 (20.4 g; 60 mmol) in hexane-anhydrous THF 1:1 (40 mL) was introduced in the reactor. The resulting system was purged with hydrogen three times at room temperature at 100 psi. The reaction was carried out at 40° C. and 4,100 kPa (600 psi) of hydrogen. When the hydrogenation reaction was completed based on GC/NMR, the reaction mixture was filtered using an internal filter in the reactor, the catalyst was rinsed one time with methylene chloride-hexane 1:1 (40 ml) with stirring and filtered again. Another portion of methylene chloride-hexane (40 mL) was added to the reactor, the reactor was pressurized with air 3,400 kPa (500 psi), and then the reactor was stirred for 30 min. The solvent was filtered off and a new loading of D.E.R. 331 in THF-hexane was introduced into the reactor to start a consecutive reaction.

TABLE IV

Data for Selected Batches (Every $3^{rd}$); Reaction Temperature 40° C., Pressure 4,100 kPa (600 psi)

| Cycle # | Reaction Time (hours) | EEW | Hydrogenation (% by NMR) |
|---|---|---|---|
| 1 | 3 | 199 | 99.5 |
| 4 | 3 | 210 | 99.0 |
| 7 | 3 | 201 | 99.4 |
| 10 | 3 | 197 | 98.7 |
| 13 | 3 | 201 | 99.2 |
| 16 | 6 | 199 | 91.4 |

Example 4—Batch Process at 2,100 kPa (300 Psi) with Catalyst Reactivation Inside a Reactor Under Pressure Bisphenol A diglycidyl ether (D.E.R. 331, 20.4 g; 60 mmol) in THF-hexane 1:1 (40 mL) was charged into a 150 mL Parr reactor along with 2.0 g of 5% Rh/C from Strem. The resulting system was purged with hydrogen three times at room temperature at 700 kPa (100 psi). The reaction was carried out at elevated temperature (see Table V) and 2,100 kPa (300 psi) of hydrogen. When the hydrogenation was completed based on GC/NMR, the reaction mixture was filtered using an internal filter in the reactor, the catalyst was rinsed one time with methylene chloride (40 ml) with stirring, and then the catalyst was filtered again. Another portion of methylene chloride (40 mL) was added to the reactor, the reactor was pressurized with air 3,400 kPa (500 psi), and the reactor contents were stirred for 30 min at 40° C. The solvent was filtered off and a new loading of D.E.R. 331 in THF-hexane was introduced into the reactor to start a consecutive reaction.

TABLE V

Data for Selected Batches (Every $3^{rd}$); Reaction Pressure 2,100 kPa (300 psi), Temperature Variable

| Cycle # | Reaction Time (hours) | EEW | Temperature (° C.) | Hydrogenation (% by NMR) |
|---|---|---|---|---|
| 1 | 6 | 191 | 40 | 99.9 |
| 4 | 4 | 207 | 50 | 98.2 |
| 7 | 4 | 201 | 50 | 96.9 |
| 10 | 4 | 203 | 55 | 99.4 |
| 13 | 4 | 202 | 60 | 92.4 |

The invention claimed is:

1. A process for at least partially reactivating the catalytic activity of at least a partially deactivated catalyst following use of the catalyst in a catalytic reaction process for hydrogenating an aromatic epoxide to produce a hydrogenated cycloaliphatic epoxide; said process comprising contacting the at least partially deactivated catalyst with an oxygen-containing source at a temperature of less than 100° C. and in the presence of a reactivation solvent for a predetermined period of time sufficient to at least partially re-oxidize and reactivate the catalyst for further use;
wherein the catalyst comprises rhodium metal, a rhodium-containing alloy, ruthenium metal, a ruthenium-containing alloy, or a combination comprising at least one of the foregoing catalysts.

2. A catalytic reaction process for hydrogenating an aromatic epoxide to produce a hydrogenated aliphatic epoxide comprising the steps of:
(a) contacting an aromatic epoxy resin with hydrogen in the presence of a catalyst comprising rhodium metal, a rhodium-containing alloy, ruthenium metal, a ruthenium-containing alloy, or a combination comprising at least one of the foregoing catalysts and a reaction solvent to initiate a hydrogenation reaction and produce a hydrogenated cycloaliphatic epoxide; such that the active catalyst deactivates after a predetermined reaction time to form at least a partially deactivated catalyst; and
(b) reactivating the deactivated catalyst by contacting the deactivated catalyst with an oxygen-containing source at a temperature of less than 100° C. and in the presence of a reactivation solvent for a pre-determined period of time sufficient to at least partially re-oxidize and reactivate the catalyst for further use.

3. The process of claim 1, wherein the catalyst is ruthenium, rhodium, or mixtures thereof.

4. The process of claim 1, wherein the catalyst is rhodium disposed on a support; and wherein the support is carbon.

5. The process of claim 1, wherein the oxygen-containing source is air.

6. The process of claim 1, wherein the step of contacting the at least partially deactivated catalyst with an oxygen-containing source is carried out at a temperature of from 20° C. to 100° C.

7. The process of claim 1, wherein the reactivation solvent is methylene dichloride.

8. The process of claim 2, wherein the reaction solvent is tetrahydrofuran or a mixture of tetrahydrofuran and hexane.

9. The process of claim 1, including further the step of washing the deactivated catalyst prior to the deactivated catalyst being contacted with an oxygen-containing source.

10. The process of claim 9, wherein the step of washing is carried out with a washing solvent; and wherein the washing solvent is methylene dichloride.

11. The process of claim 1, including further the step of wherein the reactivated catalyst is used in a catalytic hydrogenation reaction process for producing a hydrogenated cycloaliphatic epoxide from an aromatic epoxide; and the aromatic epoxide is a diglycidyl ether of 4,4'-(propane-2,2-diyl)diphenol.

12. The process of claim 2, wherein the aromatic epoxy resin is diglycidyl ether of bisphenol A; and wherein the hydrogenated cycloaliphatic epoxide is hydrogenated bisphenol A diglycidyl ether.

13. The process of claim 2, wherein the step (a) of contacting an aromatic epoxy resin with hydrogen is carried out a temperature of from 20° C. to 100° C.

14. The process of claim 2, wherein the concentration of the aromatic epoxy resin compound is from 5 weight percent to 80 weight percent; and wherein the catalyst is a metal deposited on a support and the percentage of metal on the support is from 0.2 weight percent to 50 weight percent.

15. The process of claim 1, wherein the reactivation solvent comprises an ether, a hydrocarbon, a chlorinated solvent, or a combination comprising at least one of the foregoing solvents.

16. The process of claim 1, wherein water is excluded from the reactivation solvent.

17. The process of claim 2, wherein water is excluded from the reaction solvent.

* * * * *